United States Patent [19]

Bergmann et al.

[11] Patent Number: 5,776,090
[45] Date of Patent: Jul. 7, 1998

[54] MEANS AND METHOD FOR TREATING PLANTAR FASCIITIS

[76] Inventors: Kel Bergmann, P.O. Box 8692, Rancho Santa Fe, Calif. 92067; Loren Saxton, 11142 Promesa Dr., San Diego, Calif. 92124

[21] Appl. No.: 772,907

[22] Filed: Dec. 24, 1996

[51] Int. Cl.⁶ ............................................. A61F 5/00
[52] U.S. Cl. .............................. 602/28; 602/27; 128/882
[58] Field of Search ........................... 602/5–6, 23, 24, 602/27–29; 128/882

[56] References Cited

U.S. PATENT DOCUMENTS

| | | | |
|---|---|---|---|
| 3,955,565 | 5/1976 | Johnson, Jr. ........................... | 602/12 |
| 4,217,893 | 8/1980 | Payton ................................. | 602/12 |
| 4,497,070 | 2/1985 | Cho ..................................... | 602/27 X |
| 4,774,936 | 10/1988 | Meola née Vannini ................ | 602/28 |
| 5,219,324 | 6/1993 | Hall ..................................... | 602/27 X |
| 5,441,015 | 8/1995 | Farley ................................. | 602/27 X |
| 5,507,720 | 4/1996 | Lampropoulos ..................... | 602/27 |
| 5,609,568 | 3/1997 | Andrews ............................. | 602/28 |

*Primary Examiner*—Linda C. Dvorak
*Attorney, Agent, or Firm*—Terry M. Gernstein

[57] ABSTRACT

Plantar Fasciitis is treated by placing a splint on the dorsal aspect of a wearer's foot, ankle, and fore leg and holding the wearer's foot, toes and ankle in the dorsi flexed position. This stretches the wearer's plantar fascia thus reducing symptoms over time.

15 Claims, 8 Drawing Sheets

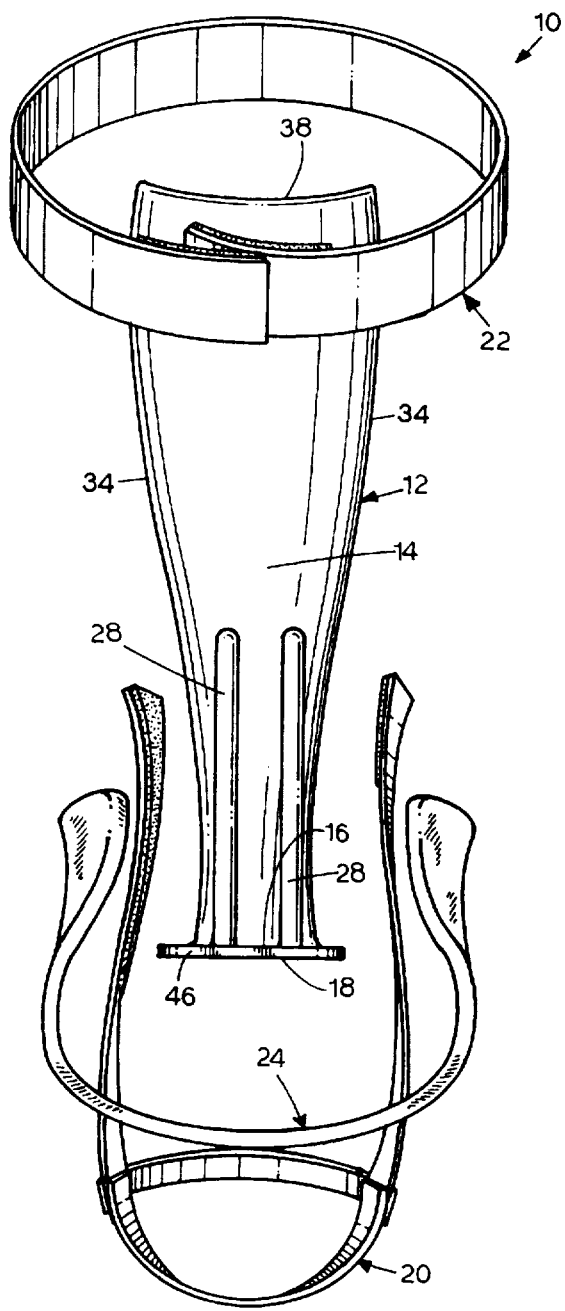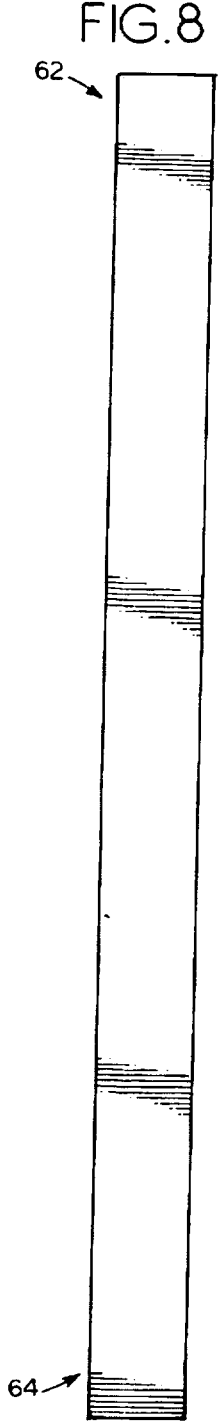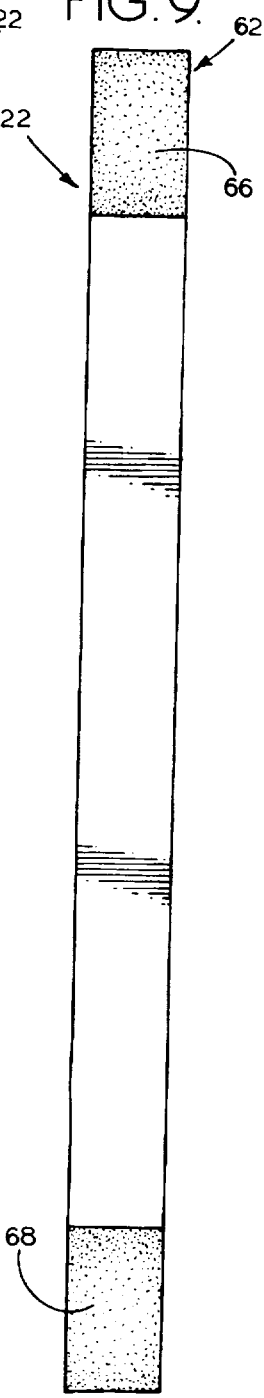

FIG. 2.
FIG. 6
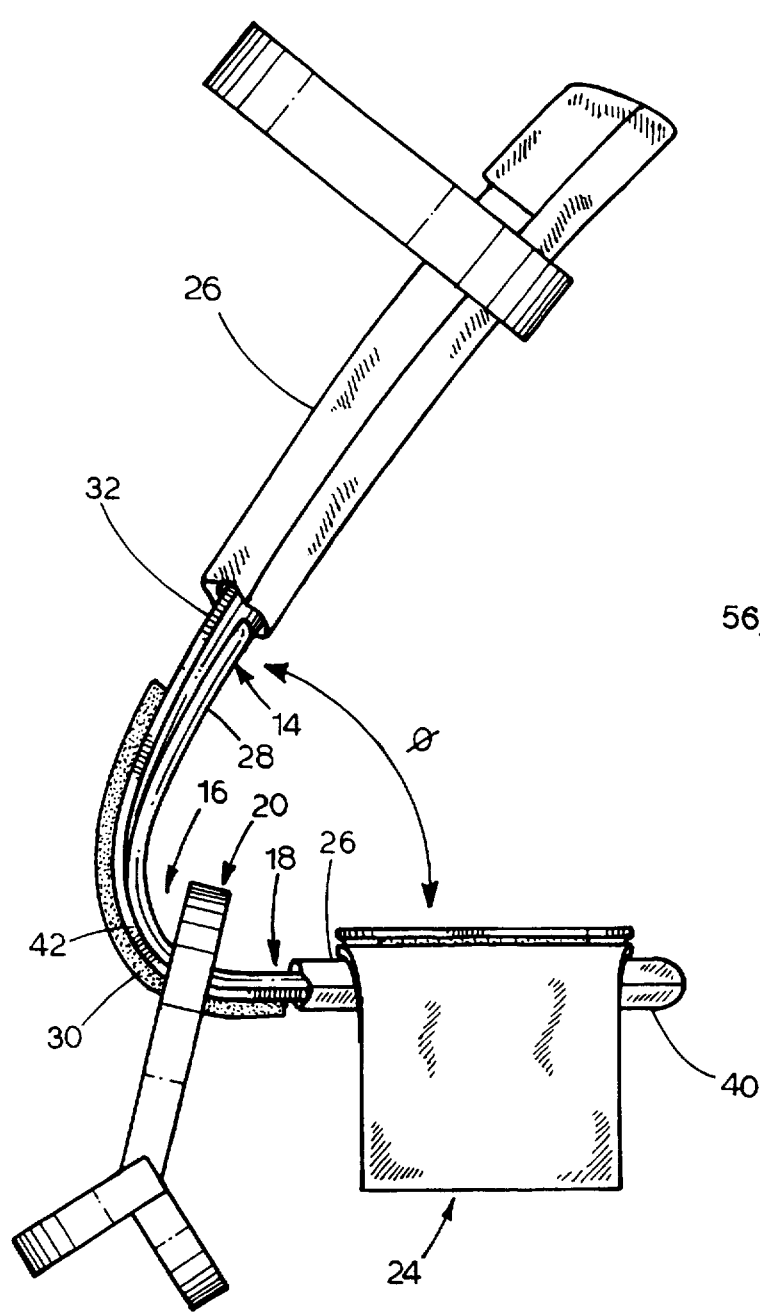
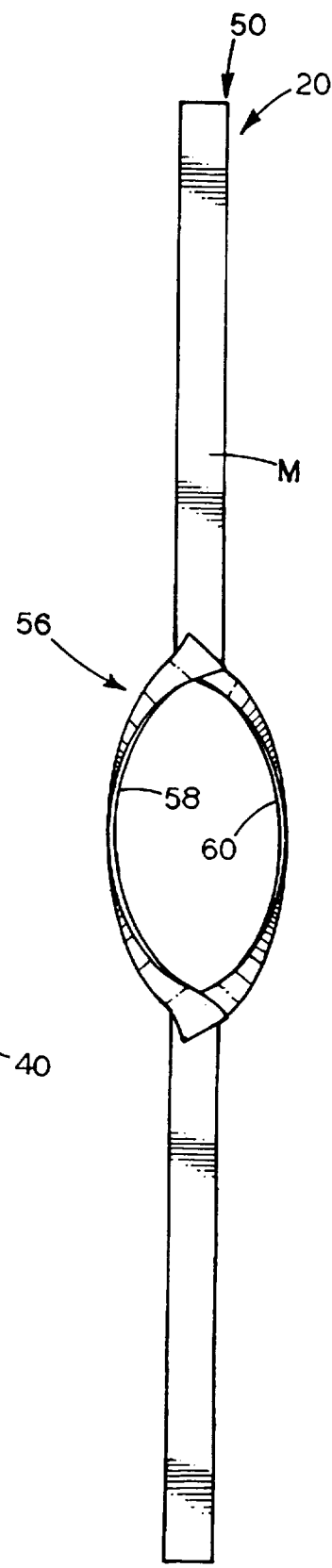

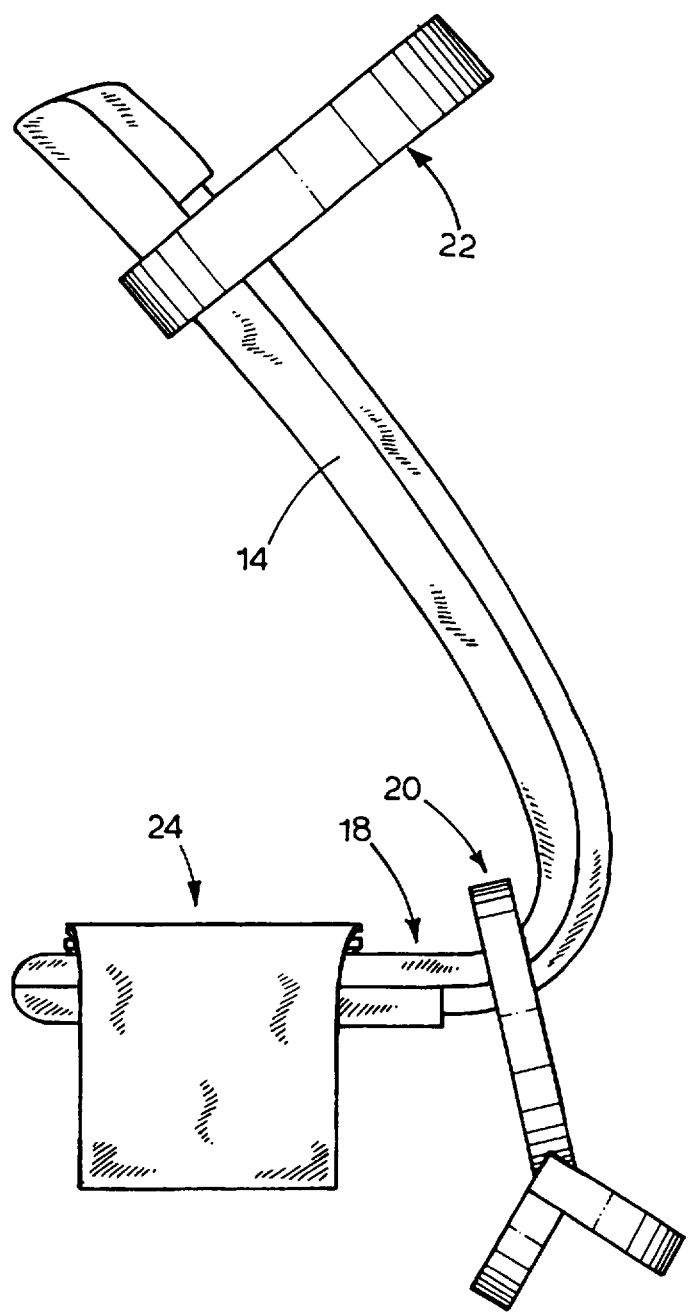
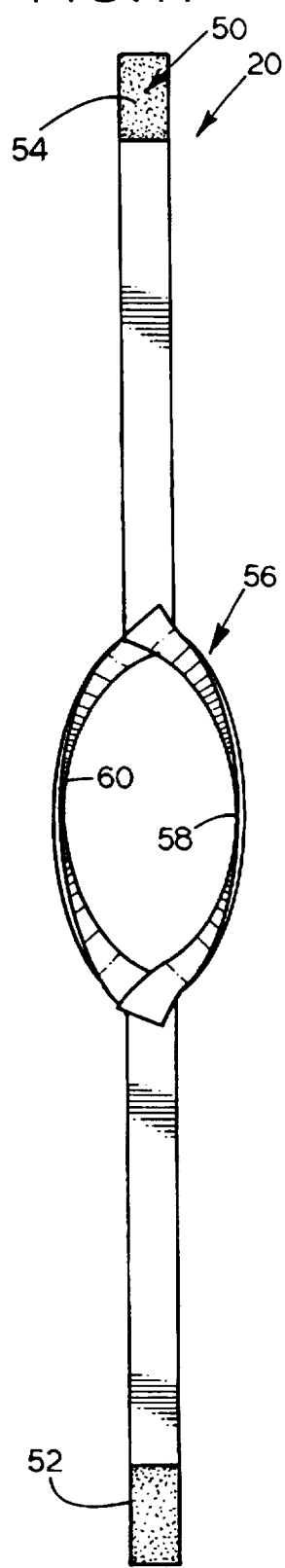

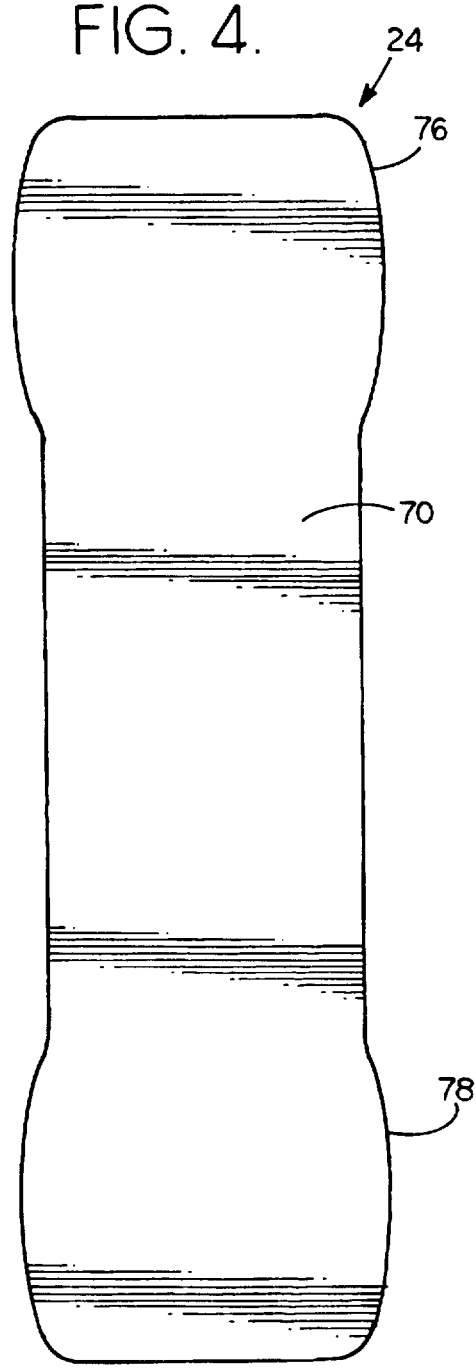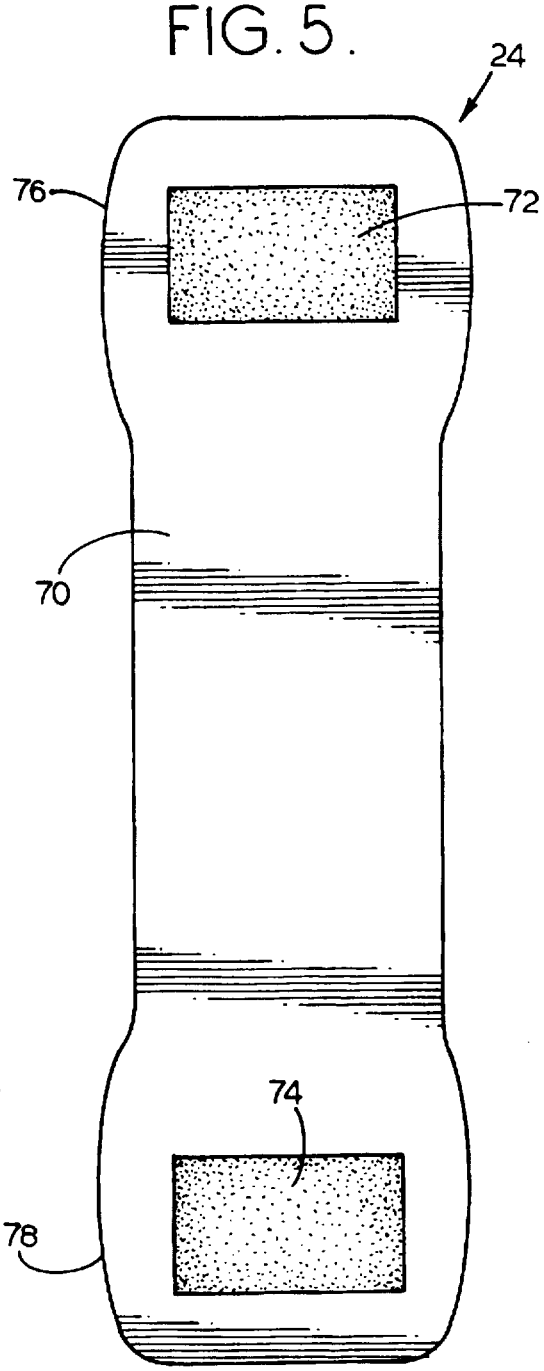

MEANS AND METHOD FOR TREATING PLANTAR FASCIITIS

TECHNICAL FIELD OF THE INVENTION

The present invention relates to the general art of orthopedic braces, and to the particular field of treating Plantar Fasciitis.

BACKGROUND OF THE INVENTION

During sleep or after prolonged sitting, a patient's foot will assume a plantar flexed position. In this position, the Achilles tendon and plantar fascia are relaxed and allowed to contract. The patient's first steps after such period of sitting or sleep cause the tissue to stretch, thus resulting in pain, that can be severe.

While the art has several devices that are intended to treat foot drop or similar conditions, such devices are not directed to treating Plantar Fasciitis. Still further, even the devices that are available at the present time have several drawbacks that inhibit their effectiveness.

For example, many of these devices are difficult to apply and wear because they are bulky. A bulky device will make ambulation difficult if not impossible as well. Still further, many of these devices are uncomfortable for the wearer and are also expensive. In addition to being bulky, some of the known devices are applied in a manner that makes ambulation difficult if not impossible.

Also, many devices are not amenable to adjustments to customize the device to the exact needs of the wearer. Therefore, there is a need for a device for treating Plantar Fasciitis that can be efficiently applied in a manner that is comfortable, yet which can be customized to the individual wearer while also permitting limited ambulation. Further, such a device should also be inexpensive.

OBJECTS OF THE INVENTION

It is a main object of the present invention to provide a means and method for treating Plantar Fasciitis.

It is another object of the present invention to provide a means and method for treating Plantar Fasciitis which is efficient to apply and comfortable for the wearer.

It is another object of the present invention to provide a means and method for treating Plantar Fasciitis which permits limited ambulation while wearing the device.

It is another object of the present invention to provide a means and method for treating Plantar Fasciitis which can be customized to the individual wearer.

It is another object of the present invention to provide a means and method for treating Plantar Fasciitis which is not bulky.

It is another object of the present invention to provide a means and method for treating Plantar Fasciitis which is inexpensive.

SUMMARY OF THE INVENTION

These, and other, objects are achieved by a means and a method for treating Plantar Fasciitis which includes a splint means worn on the dorsal aspect of a wearer's foot, ankle and fore leg for holding the wearer's foot, toes and ankle in a dorsi flexed position and stretching the wearer's plantar fascia.

The device holds the foot, toes and ankle in a dorsi flexed position while the wearer is sleeping or sitting and at the same time stretches the plantar fascia. It will also allow ambulation, to the bathroom or in emergency situations, for example, without removing the device. The dorsiflexion angle can be adjusted to fit the particular wearer.

More specifically, the device has a dynamic action to pull the wearer's foot and toes toward the front of the wearer's shin to form an acute angle between the foot and the front of the shin. The device includes adjustable straps to hold it on the wearer and the device can be used on either the right or the left side.

Because of the structure of the device, the device permits adjustment of the fit to customize it to the particular wearer, without being bulky or uncomfortable and while permitting efficient application. Still further, due to the structure of the device, ambulation is possible without removing the device. The device is also inexpensive.

BRIEF DESCRIPTION OF THE DRAWING FIGURES

FIG. 1 is a front elevational view of the device for treating Plantar Fasciitis embodying the present invention with a cover removed.

FIG. 2 is a side view thereof with the cover partially shown.

FIG. 3 is a side view thereof showing the side opposite to the side shown in FIG. 2.

FIG. 4 is a top plan view of the toe strap of the device.

FIG. 5 is a bottom plan view of the toe strap.

FIG. 6 is a top plan view of the heel strap of the device.

FIG. 7 is a bottom plan view of the heel strap.

FIG. 8 is a top plan view of a calf strap of the device.

FIG. 9 is a bottom plan view of the calf strap.

DETAILED DESCRIPTION OF THE PREFERRED EMBODIMENT OF THE INVENTION

Figure 5A:
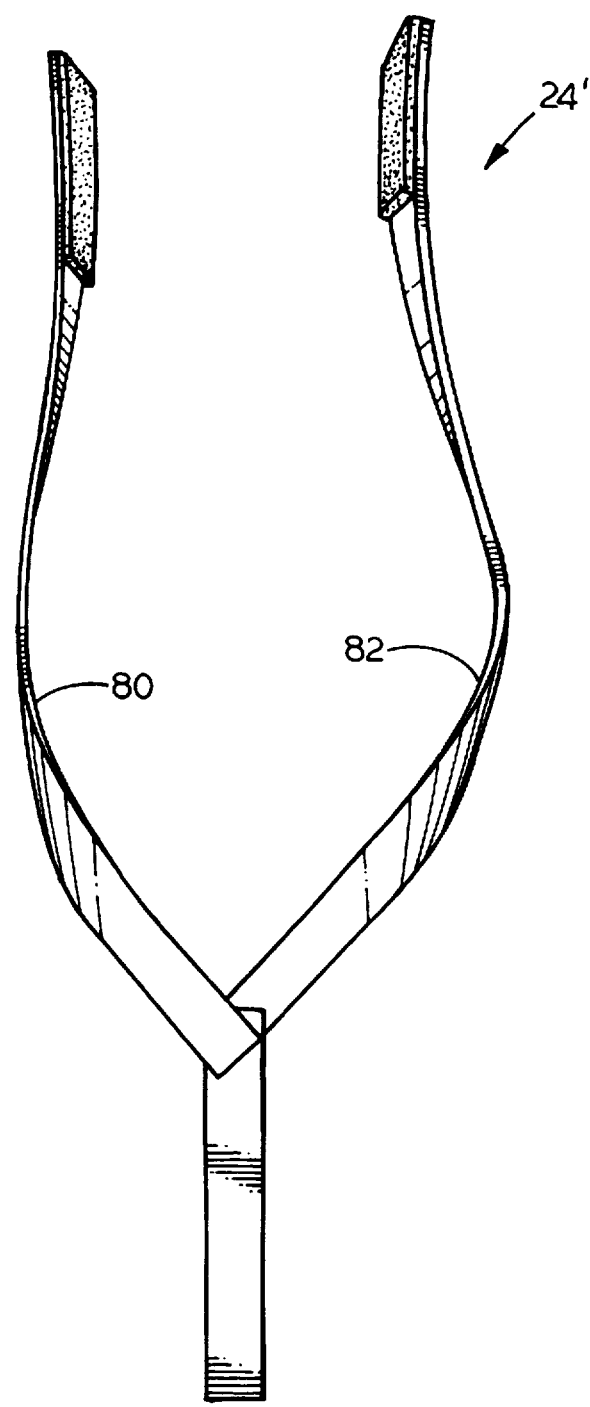
FIG. 5A shows an alternative form of the toe strap.
Figure 11:
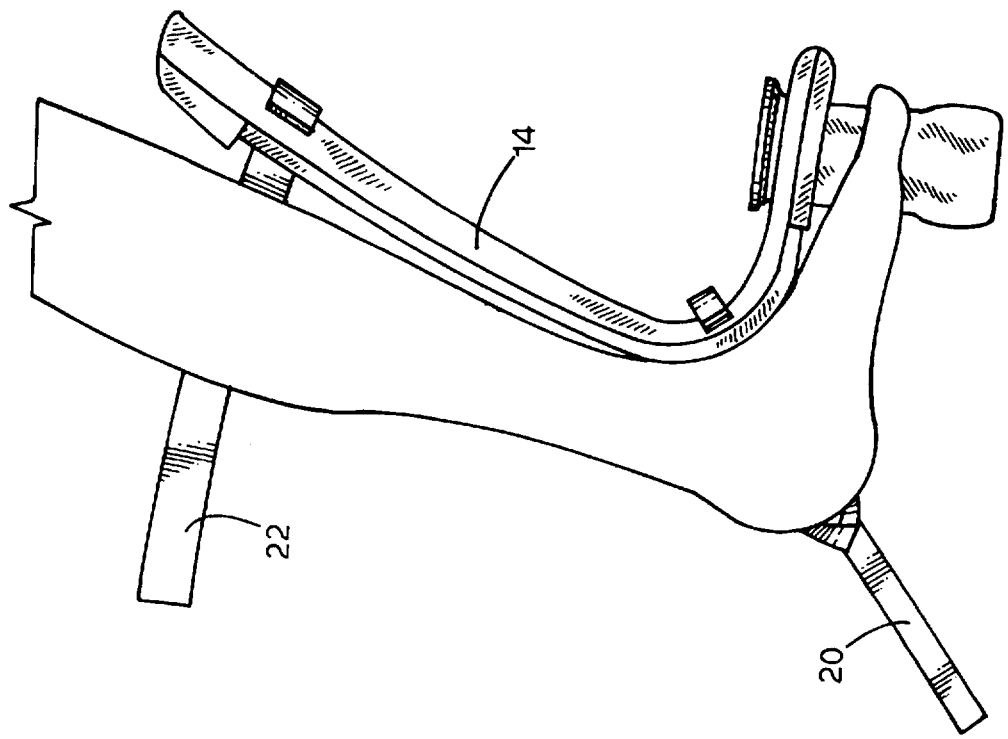
FIGS. 10–15 show steps in the method of treating Plantar Fasciitis embodying the present invention, with a narrow toe strap being shown in FIG. 10 for the sake of completeness.

Shown in FIGS. 1–3 is a preferred form of a device 10 for treating Plantar Fasciitis of the present invention. Broadly, device 10 includes a splint 12 which is applied to a user (not shown in FIGS. 1–3) to engage the front surface of the shin and which includes a fore leg-engaging portion 14, an ankle-engaging portion 16 and a foot-engaging portion 18. The device is located to be worn on the dorsal aspect of the wearer's foot, ankle and fore leg for holding the wearer's foot, toes and ankle in a dorsi flexed position and for stretching the wearer's plantar fascia. Device 10 further includes means for adjustably attaching the splint to the wearer. Broadly, the means for attaching the splint to the wearer includes a heel strap 20, a calf strap 22 and a toe strap 24. A cloth cover, generally indicated at 26 (see FIG. 2), covers the splint.

The cover is shown in place in FIG. 2 and has the straps attached thereto. The cover is formed of material that is comfortable to the wearer, yet can be easily cleaned. The cover includes closure flaps 27A and 27B so the cover can be placed on the splint 12 and easily removed therefrom.

More specifically, splint 12 is one-piece and is formed of plastic, but could also be formed of metal. The material of the splint can be bent adjacent to ankle portion 16 and has a material memory that permits it to maintain the position and angular orientation under the conditions of use of device 10. The material of splint 12 permits comfortable wearing, even for patients having a restricted range of motion, yet is stiff enough to support the patient's foot as desired. Specifically, ankle-engaging portion 16 can be bent so angle θ formed between fore leg-engaging portion 14 and foot-engaging portion 18 can be adjusted to form an acute angle as shown in FIG. 2. Adjustment of angle θ permits the device to be customized for the particular wearer as will be understood by those skilled in the art based on the teaching of this disclosure. Ankle-engaging portion 16 includes two stiffening ribs 28 that permit the angle portion to be bent as just discussed, while still retaining sufficient stiffness to achieve the objective of supporting the wearer's foot in the manner discussed herein. A pad 30 of soft cushioning material is mounted on rear surface 32 of splint 12 adjacent to the ankle-engaging portion to provide comfort to the wearer. Pad 30 also permits the wearer to walk with device 10 in place on his or her leg and foot.

Rear surface 32 is curved so it can comfortably engage the front surface of the wearer's shin, and sides 34 thereof diverge upwardly from ankle-engaging portion 16 to top edge 38 to provide further fit to the device.

As mentioned above, rear surface 32 is arcuate; however, bottom surface 40 of foot-engaging portion 18 is essentially planar. Therefore, there is a ribbed section 42 on the ankle-engaging portion which merges the arcuate surface 32 smoothly into the planar surface 42. This section also contributes to the flexibility and material memory of the ankle-engaging portion. The ribs 30, along with the ribbed section 42 combine to form a means for retaining a desired angle θ between the wearer's foot and the wearer's fore leg.

The foot engaging section is sized to have edge 46 thereof located adjacent to the wearer's toes so free movement of the toes is possible.

Heel strap 20 is best shown in FIGS. 6 and 7 and is attached to cover 26 to extend around the wearer's heel and hold that heel to the device. Heel strap 20 includes one end 50 attached to the cover by hook-and-loop fastener elements adjacent to the ankle-engaging portion and has another end 52 which can be attached to the cover or to the heel strap by hook-and-loop fastener elements. The heel strap includes a patch 54 of fastener material on each end, and the remaining body of the heel strap is formed of material M to which the patches of fastener material easily adhere whereby the length of the heel strap can be adjusted. The heel strap can also be removed from the cover to facilitate cleaning. Heel strap 20 further includes a sling portion 56 which is formed by two arcuate straps 58 and 60 that are sized to engage the wearer's heel. As can be understood by one skilled in the art from this disclosure, once the heel strap is in place, the wearer's heel is snugly, yet comfortably, held in the device 10. However, due to the adjustability of the length of the heel strap, the amount of snugness can be adjusted to fit the particular wearer. Material M is used on all elements of the cover 26 and the associated straps so patches of hook-and-loop fastener material can be attached as needed for proper fastening.

As shown in FIGS. 8 and 9, calf strap 22 is elongate and, as shown in FIG. 1, is attached to cover 26 at one end 62 and has the other end 64 free to extend around the wearer's calf. Strap 22 has patches 66 and 68 of hook-and-loop material for releasably attaching these ends to the body of the strap which is formed of material that releasably mates with the material in the patches whereby the length of strap 22 can be adjusted to facilitate adjustable attachment of device 10 to the wearer's leg. By altering the length of strap 22, the amount of tension on the wearer's fore leg can be altered and the amount of pressure placed on that leg by device 10 can be adjusted to fit the needs of the individual wearing the device. Strap 22 can be completely removed from cover 26 to facilitate cleaning.

The toe strap 24 is best shown in FIGS. 4 and 5, and includes a body 70 of cloth-like material, with patches 72 and 74 of fastener material on that body adjacent to ends 76 and 78 respectively. As with the other elements of device 10, the cloth-like material is formed to releasably mate with the fastener material, which can be hook-and-loop material. The length of toe strap 24 is adjustable so it can be tied around the wearer's foot and the foot-engaging portion to securely hold that foot-engaging portion to the dorsal aspect of the wearer's foot.

An alternative form 24' of toe strap 24 is shown in FIG. 5A and includes two straps 80 and 82 each attached at one end thereof to the cover adjacent to the foot-engaging portion and having another end thereof free. As is the case with all other straps, straps 80 and 82 have patches of releasable fastener material at each end and a body of cloth-like material that cooperates with these patches of fastener material so the straps can be attached to themselves at nearly any position on the body portion thereof. Toe strap 24' is secured to the wearer's toes and to the wearer's foot to attach foot-engaging portion 18 to the dorsal aspect of the wearer's foot.

Figure 10:
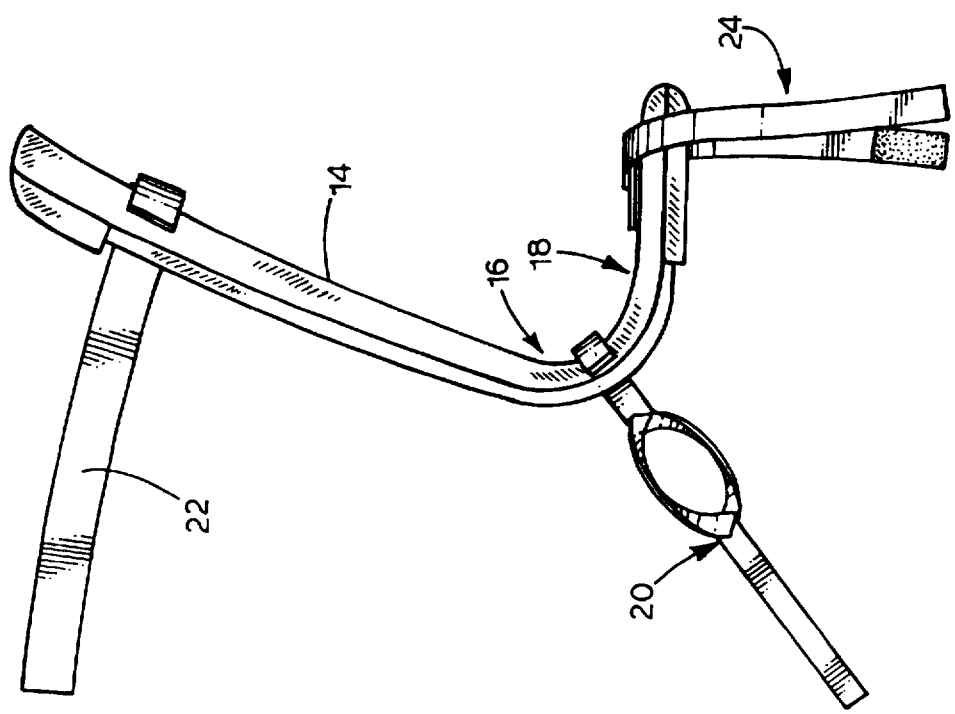
Figure 13:
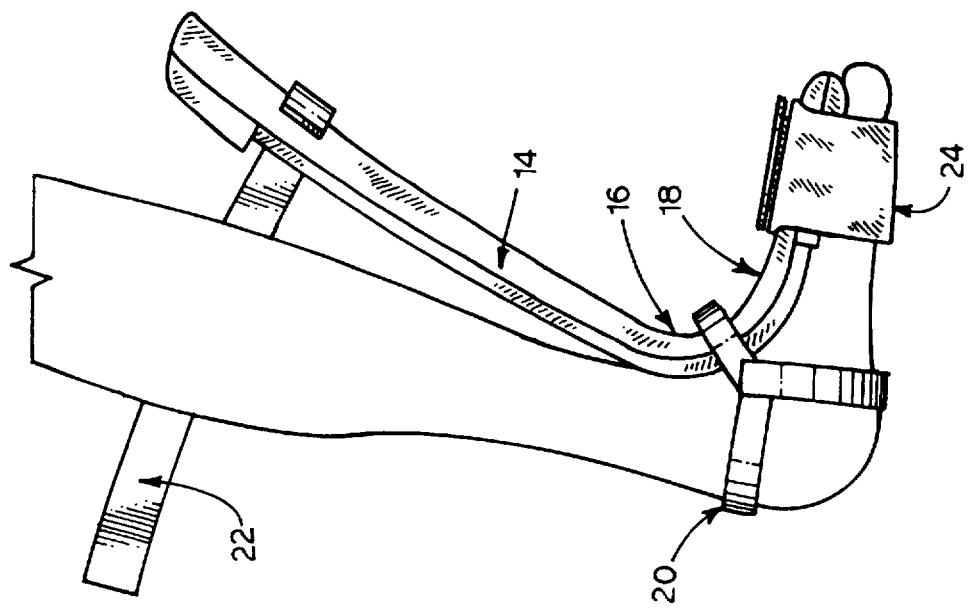

The method of treating Plantar Fasciitis using the above-described device 10 is illustrated in FIGS. 10-15 to which attention is now directed. It is noted that FIG. 10 shows a narrow toe strap for the sake of completeness. Broadly, the method includes providing device 10, positioning device 10 on top of the wearer's foot adjacent to the front of the wearer's shin and adjacent to the top of the wearer's ankle; placing the wearer's weight on the wearer's foot; moving the front of the wearer's shin forward toward the splint means; and attaching the device to the wearer.

Figure 12:
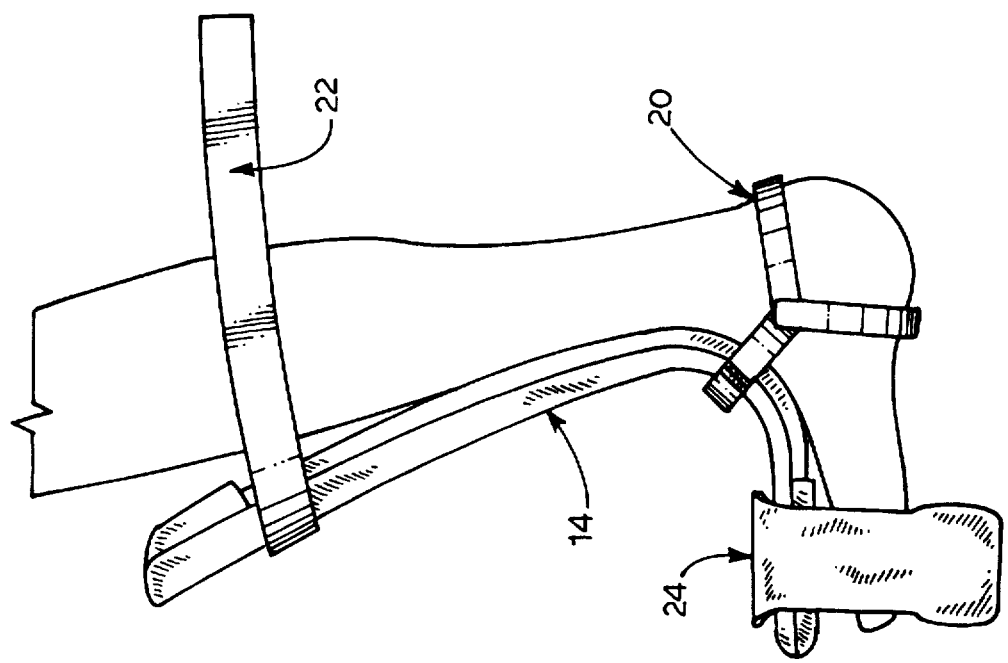
Figure 15:
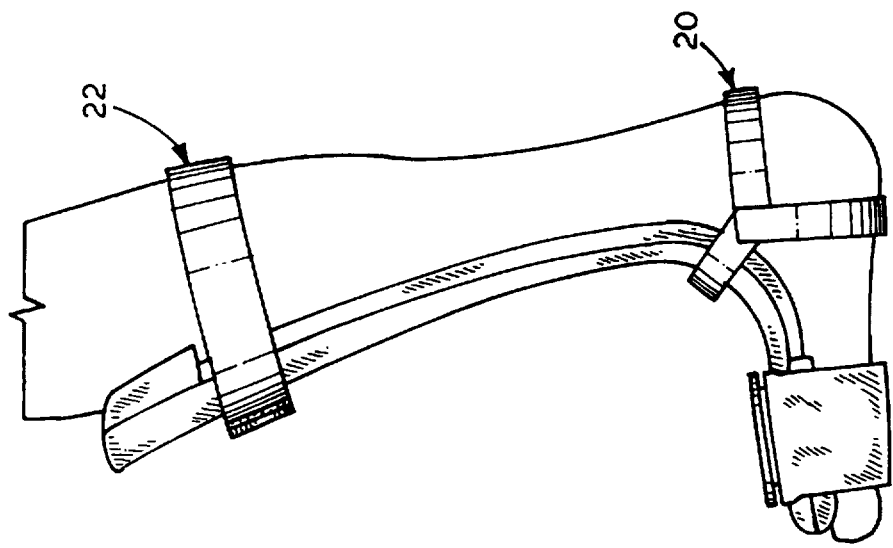
Figure 14:
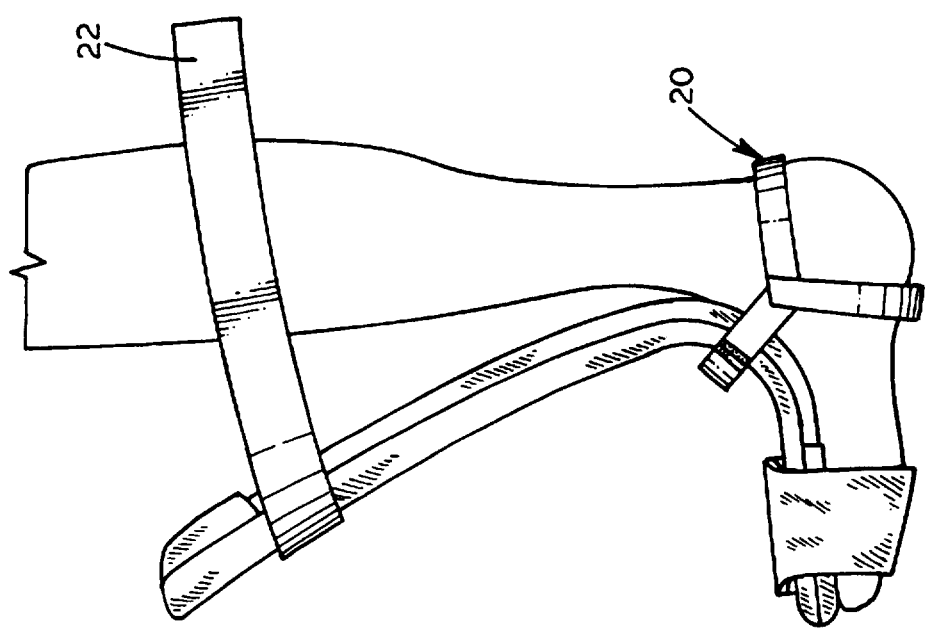

More specifically, the method includes placing a cotton blend sock over the patient's foot and leg; then placing the patient in a sitting position. While the patient is in the sitting position, the device 10 is placed on top of the foot with the angle section of the device adjacent to the ankle-engaging portion in the angle of the wearer's ankle (see FIG. 11). Heel sling 20 is then secured to the patient's heel as indicated in FIG. 12. Toe strap 24 or 24' is secured to the patient's foot. If strap 24' is used, one strap thereof is secured under the patient's toes and the other strap is secured to the patient's foot. The toe strap is secured in FIGS. 13 and 14.

The patient then places his or her weight on the foot and heel. The leg is then forced forward until the shin touches the device 10, and the calf strap 22 is secured around the leg, see FIG. 15. The desired angle θ is set by bending the device at ankle-engaging portion 16 and adjusting the tension of calf strap 22.

The dorsal design of the invention allows for limited night-time ambulation; its semi-rigid, pre-loaded construction allows for some ankle motion throughtout the night, thereby increasing patient compliance; it provides dynamic stretch through plastic elasticity; it places the patient's foot in position of dorsi flexion to facilitate stretch of plantar fascia; it is well padded for comfort; it is simple to apply; it can be easily manufactured in various sizes, including small and regular; and it can fit on either the right or the left leg.

It is understood that while certain forms of the present invention have been illustrated and described herein, it is not to be limited to the specific forms or arrangements of parts described and shown.

We claim:

1. A device for treating Plantar fasciitis comprising:
   A) a one-piece splint worn on a wearer's leg for stretching a wearer's plantar fascia and including
      (1) a fore leg-engaging portion that engages the dorsal aspect of the wearer's leg when said splint is in place,
      (2) an ankle-engaging portion that engages the dorsal aspect of the wearer's ankle when said splint is in place,
      (3) a foot-engaging portion that engages the dorsal aspect of the wearer's foot when said splint is in place;
   B) a heel strap having one end thereof anchored to said splint near said ankle-engaging portion, another end having fastening means thereon for attaching said heel strap to itself, said heel strap including a heel sling portion that engages the wearer's heel when said splint is in place;
   C) a calf strap having one end thereof anchored to said fore leg-engaging portion and another end having fastening means thereon for attaching said calf strap to itself;
   D) a toe strap having fastening means thereon for attaching said toe strap to itself and to the wearer's foot;
   E) said splint being formed of a material that will maintain a selected angular orientation between the wearer's foot and the wearer's foreleg when said splint is in place, said foot-engaging portion and said fore leg-engaging portion forming an acute angle with each other to cause the wearer's foreleg and foot to form an acute angle between them to pull the wearer's foot toward the wearer's foreleg when the splint is in place whereby the wearer's ankle and foot are held in a dorsi-flexed position for stretching the wearer's plantar fascia.

2. The device defined in claim 1 wherein all of said fastening means include hook-and-loop fastening elements.

3. The device defined in claim 1 further including a cloth covering on said splint.

4. The device defined in claim 1 wherein said toe strap includes two portions.

5. The device defined in claim 1 further including stiffening ribs in said ankle-engaging portion.

6. The device defined in claim 1 further including a pad on said ankle-engaging portion.

7. The device defined in claim 1 further including a cover element.

8. The device defined in claim 7 further including flaps on said cover.

9. A device for treating Plantar Fasciitis comprising:
   A) a splint means worn on the dorsal aspect of a wearer's foot, ankle and fore leg for holding the wearer's foot, toes and ankle in a dorsi flexed position and forming an acute angle between the wearer's foot and foreleg so that the wearer's leg and foot are forced toward each other to form an acute angle when the splint is in place and stretching the wearer's plantar fascia; and
   B) strap means anchored to said splint means for attaching said splint to the wearer and for adjusting the angle formed between the wearer's foot and the wearer's fore leg when the splint means is attached to the wearer.

10. The device defined in claim 9 further including means for retaining a desired angle between the wearer's foot and the wearer's fore leg when the device is in place.

11. A method for treating Plantar Fasciitis comprising:
    A) providing a device for treating Plantar Fasciitis which includes a one-piece splint worn on a wearer's leg and including a fore leg-engaging portion that engages the dorsal aspect of the wearer's leg when said splint is in place, an ankle-engaging portion that engages the dorsal aspect of the wearer's ankle when said splint is in place, a foot-engaging portion that engages the dorsal aspect of the wearer's foot when said splint is in place; a heel strap having one end thereof anchored to said splint near said ankle-engaging portion, another end having fastening means thereon for attaching said heel strap to itself and a heel sling portion that engages the wearer's heel when said splint is in place; a calf strap having one end thereof anchored to said fore leg-engaging portion and another end having fastening means thereon for attaching said calf strap to itself; and a toe strap having fastening means thereon for attaching said toe strap to itself and to the wearer's foot;
    B) positioning the device on top of the wearer's foot with the ankle-engaging portion adjacent to the angle of the wearer's ankle;
    C) extending the heel strap about the wearer's heel and securing the heel strap to the splint;
    D) extending the toe strap around the wearer's foot and securing the toe strap in place about the wearer's foot and the foot-engaging portion;
    E) placing the wearer's weight on the wearer's foot and heel;
    F) bending the wearer's leg forward until the wearer's shin touches the leg-engaging portion and forming an acute angle between the wearer's fore leg and the wearer's foot and forcing the wearer's leg and foot forward toward each other and stretching the wearer's plantar fascia; and
    G) extending the calf strap around the wearer's calf and securing the calf strap to the fore leg-engaging portion.

12. A method for treating Plantar Fasciitis comprising:
    A) providing a device for treating Plantar Fasciitis which includes a splint means worn on the dorsal aspect of a wearer's foot, angle and fore leg for holding the wearer's foot, toes and ankle in a dorsi flexed position and stretching the wearer's plantar fascia; and means anchored to said splint means for attaching said splint to the wearer and for adjusting the angle formed between the wearer's foot and the wearer's fore leg when the splint means is attached to the wearer;
    B) positioning the splint means on top of the wearer's foot adjacent to the front of the wearer's shin and adjacent to the top of the wearer's ankle;
    C) placing the wearer's weight on the wearer's foot;
    D) moving the front of the wearer's shin forward toward the splint means and forming an acute angle between the wearer's fore leg and the wearer's foot and forcing the wearer's leg and foot forward toward each other and stretching the wearer's plantar fascia; and
    E) attaching the device to the wearer.

13. The method defined in claim 12 wherein the step of moving the front of the wearer's shin forward toward the splint means further includes a step of adjusting the position of the wearer's leg relative to the splint means to adjust the angle between the wearer's foot and the wearer's fore leg.

14. A device for treating Plantar fasciitis comprising:
    A) a one-piece splint worn on a wearer's leg and including
       (1) a fore leg-engaging portion that engages the dorsal aspect of the wearer's leg when said splint is in place,
       (2) an ankle-engaging portion that engages the dorsal aspect of the wearer's ankle when said splint is in place, (3) a foot-engaging portion that engages the dorsal aspect of the wearer's foot when said splint is in place;

B) a heel strap having one end thereof anchored to said splint near said ankle-engaging portion, another end having fastening means thereon for attaching said heel strap to itself and a heel sling portion that engages the wearer's heel when said splint is in place;

C) a calf strap having one end thereof anchored to said fore leg-engaging portion and another end having fastening means thereon for attaching said calf strap to itself;

D) a toe strap having fastening means thereon for attaching said toe strap to itself and to the wearer's foot; and E) said fore leg-engaging portion being oriented at an acute angle with said foot-engaging portion so that the wearer's leg and foot are forced forward toward each other to form an acute angle when the device is in place.

15. A device for treating Plantar fasciitis comprising:

A) a one-piece splint worn on a wearer's leg and including
 (1) a fore leg-engaging portion that engages the dorsal aspect of the wearer's leg when said splint is in place,
 (2) an ankle-engaging portion that engages the dorsal aspect of the wearer's ankle when said splint is in place,
 (3) a foot-engaging portion that engages the dorsal aspect of the wearer's foot when said splint is in place;

B) a heel strap having one end thereof anchored to said splint near said ankle-engaging portion, another end having fastening means thereon for attaching said heel strap to itself and a heel sling portion that engages the wearer's heel when said splint is in place;

C) a calf strap having one end thereof anchored to said fore leg-engaging portion and another end having fastening means thereon for attaching said calf strap to itself;

D) a toe strap having fastening means thereon for attaching said toe strap to itself and to the wearer's foot; and E) said splint being formed of a material that can be adjusted adjacent to said ankle-engaging portion to orient said fore leg-engaging portion at an angle with said foot-engaging portion and will maintain that angle when the device is in place on the wearer so that the wearer's leg and foot are forced forward toward each other to form a corresponding angle when the device is in place.

\* \* \* \* \*